(12) United States Patent
Masson

(10) Patent No.: US 8,247,620 B2
(45) Date of Patent: Aug. 21, 2012

(54) PRODUCTION OF HIGHLY PURE HYDROQUINONE

(75) Inventor: Jean-Claude Masson, Lyons (FR)

(73) Assignee: Rhodia Operations, Aubervilliers (FR)

( * ) Notice: Subject to any disclaimer, the term of this patent is extended or adjusted under 35 U.S.C. 154(b) by 445 days.

(21) Appl. No.: 12/310,661

(22) PCT Filed: Sep. 3, 2007

(86) PCT No.: PCT/FR2007/001424
§ 371 (c)(1), (2), (4) Date: Jan. 12, 2010

(87) PCT Pub. No.: WO2008/029018
PCT Pub. Date: Mar. 13, 2008

(65) Prior Publication Data
US 2010/0152495 A1    Jun. 17, 2010

(30) Foreign Application Priority Data

Sep. 4, 2006 (FR) ...................................... 06 07730

(51) Int. Cl.
*C07C 37/84* (2006.01)

(52) U.S. Cl. ......... 568/750; 568/751; 568/752; 568/753

(58) Field of Classification Search ........... 568/750–753
See application file for complete search history.

(56) References Cited

U.S. PATENT DOCUMENTS

| 1,908,817 A * | 5/1933 | Britton et al. ................. 568/750 |
| 3,849,502 A | 11/1974 | Bourdin et al. |
| 3,953,528 A | 4/1976 | Inada et al. |
| 4,072,721 A * | 2/1978 | Sturm et al. .................. 568/753 |
| 4,308,110 A | 12/1981 | Hosaka et al. |
| 4,396,783 A | 8/1983 | Esposito et al. |
| 6,441,258 B1 | 8/2002 | Cately |
| 6,844,472 B1 | 1/2005 | Bourdon et al. |

FOREIGN PATENT DOCUMENTS

| FR | 2 071 464 A5 | 9/1971 |
| FR | 2 121 000 A5 | 8/1972 |
| FR | 2 200 227 A1 | 4/1974 |
| FR | 2 467 185 A1 | 4/1981 |
| FR | 2 489 816 A1 | 3/1982 |
| FR | 2 788 763 A1 | 7/2000 |
| FR | 2 856 681 A1 | 12/2004 |
| GB | 1332420 A | 10/1973 |
| JP | 51 039 636 A | 4/1976 |
| SU | 1 502 559 A1 | 8/1989 |
| WO | WO 00/23185 | 4/2000 |
| WO | WO 00/23377 | 4/2000 |

OTHER PUBLICATIONS

International Search report PCT/FR2007/001424 dated Feb. 12, 2008.

* cited by examiner

*Primary Examiner* — Brian J Davis
(74) *Attorney, Agent, or Firm* — SNR Denton US LLP

(57) ABSTRACT

A process for preparing highly pure hydroquinone freed of the impurities resulting from the production thereof includes at least the following steps: a) the crude hydroquinone in a liquid form and comprising at least resorcin and pyrogallol as impurities is subjected to a controlled cooling ensuring the crystallization of pure hydroquinone, b) the pure hydroquinone crystals are separated from the mother liquors, c) heating and partial melting thereof is next is carried out, d) the purified hydroquinone is then completely melted, and e) the purified hydroquinone is recovered.

24 Claims, 2 Drawing Sheets

PRODUCTION OF HIGHLY PURE HYDROQUINONE

CROSS-REFERENCE TO PRIORITY/PCT APPLICATIONS

This application claims priority under 35 U.S.C. §119 of FR 0607730, filed Sep. 4, 2006, and is a continuation/national phase of PCT/FR 2007/001424, filed Sep. 3, 2007 and designating the United States (published in the French language on Mar. 13, 2008, as WO 2008/029018 A1; the title and abstract were also published in English), each hereby expressly incorporated by reference in its entirety and each assigned to the assignee hereof.

A subject matter of the present invention is a process for the preparation of highly purified hydroquinone, said process in particular making it possible to access various degrees of high purity.

The invention is targeted at providing hydroquinone freed from the impurities resulting from its process of preparation.

Hydroquinone (or 1,4-dihydroxybenzene) is a product widely used in numerous fields of application as polymerization inhibitor or antioxidant in elastomers or as synthetic intermediate. Another field of application is photography. It follows that this is a staple.

Varying purities are required according to the markets concerned.

This is because, if some applications, in particular photography, require a very high degree of purity, others are satisfied with a technical hydroquinone, that is to say a hydroquinone having a lower degree of purity, in order to minimize the operating costs.

Thus, hydroquinone has to satisfy variable purity requirements which can in some cases be fairly restrictive.

The problem which is posed is that hydroquinone is not easy to purify as it is an oxidation-sensitive product which quickly results in decomposition products which are colored.

Furthermore, different physicochemical characteristics, in terms of particle size, flowability or rate of dissolution, may be required depending on the applications.

Thus, the market requires diversified products having a good chemical stability on storage.

One of the synthetic routes to hydroquinone consists in carrying out hydroxylation of phenol by hydrogen peroxide, in particular in the presence of homogeneous or heterogeneous acid catalysts.

Thus, recourse may be had, as according to FR 2 071 464, to a strong protic acid, that is to say an acid exhibiting a pKa in water of less than 0.1, preferably of less than −1.

Mention may be made, as examples of strong protic acids, inter alia, of sulfuric acid, chlorosulfuric acid, perchloric acid or sulfonic acids, such as, for example, methanesulfonic, trifluoromethanesulfonic, toluenesulfonic or phenol-sulfonic acid.

Mention may be made, as other examples of protic acid catalysts, of sulfonic resins and more particularly resins sold under various trade names. Mention may be made, inter alia, of the following resins: Temex 50, Amberlyst 15, Amberlyst 35, Amberlyst 36 and Dowex 50W.

The abovementioned resins are composed of a polystyrene backbone which carries functional groups which are sulfonic groups. The polystyrene backbone is obtained by polymerization of styrene and divinylbenzene under the influence of an activation catalyst, generally an organic peroxide, which results in a crosslinked polystyrene which is subsequently treated with concentrated sulfuric or sulfochloric acid, resulting in a sulfonated styrene/divinylbenzene copolymer.

It is also possible to resort to sulfonic resins which are phenol/formaldehyde copolymers and which carry, on the aromatic ring, a methylenesulfonic group, for example the resin sold under the name Duolite ARC 9359.

Other commercially available resins are also suitable and mention may be made of perfluorinated resins carrying sulfonic groups and more particularly Nafion, which is a copolymer of tetrafluoroethylene and of perfluoro[2-(fluorosulfonylethoxy)propyl]vinyl ether.

Mention may be made, as other catalysts suitable in hydroxylation processes, of iron(II) and copper(II) complexes (FR 2 121 000, SU 1 502 559) and any other catalyst of Fenton type.

Other processes for the preparation of hydroquinone involve heterogeneous catalysis. Thus, it is possible to employ an acid zeolite of titanium silicalite (or titanosilicalite-1) type or of iron silicalite type of TS-1 type (FR 2 489 816), a zeolite of MEL titanium silicalite type (EP 1 131 264) or a titanozeosilite of MFI type (EP 1 123 159). It is also possible to use an MCM-22 zeolite (FR 2 856 681).

On conclusion of such hydroxylation reactions, a mixture is obtained essentially comprising pyrocatechol (or 1,2-dihydroxybenzene) and hydroquinone in variable proportions, generally with a pyrocatechol/hydroquinone ratio by weight of the order of 0.25 to 4.0, and also various byproducts in much smaller amounts, in particular resorcinol (or resorcin or also 1,3-dihydroxybenzene) and trihydroxybenzenes, more particularly pyrogallol (or 1,2,3-trihydroxybenzene), generally at contents of the order of 0.5% to 4.0% by weight, percentages expressed with respect to the amount of hydroquinone and of pyrocatechol (or pyrocatechin) formed.

Mixtures with variable compositions, comprising, by weight, from 20% to 80% of pyrocatechol, from 80% to 20% of hydroquinone, from 0.1% to 2% of resorcinol and from 0.1% to 2% of pyrogallol, are obtained.

Typically, mixtures comprising, by weight, from 50 to 80% of pyrocatechol, from 20 to 50% of hydroquinone, from 0.1 to 2% of resorcinol and from 0.1 to 2% of pyrogallol are obtained.

In order to isolate the hydroquinone from crude mixtures of this type, one currently known method consists in distilling said mixture, making it possible to obtain, at the distillation top, pyrocatechol (which is the most volatile compound of the mixture) and, at the distillation bottom, a "crude hydroquinone" $HQ^0$, namely a mixture essentially comprising hydroquinone in combination with small amounts of impurities (resorcinol and pyrogallol, and also possible traces of pyrocatechol not removed by the distillation).

Other processes for the synthesis of hydroquinone consist of the oxidation of 1,4-diisopropylbenzene with, as byproduct, 1,2- and/or 1,3-dihydroxybenzene (pyrocatechol and resorcinol), in the absence of compounds of trihydroxybenzene type, such, as pyrogallol. Thus, the document FR 2 788 763 describes the preparation of crude hydroquinone comprising dihydroxylated impurities, pyrocatechol and resorcin. The pyrocatechol is removed by distillation and then the purified hydroquinone is obtained by melt bath refining the hydroquinone/resorcin binary mixture.

The invention provides a process which makes it possible to obtain a hydroquinone having the desired purity.

Thus, one object of the invention is to provide a process for the purification of crude hydroquinone in which impurities of dihydroxybenzene and trihydroxybenzene type are present simultaneously.

Another object of the invention is to provide a flexible process which makes it possible to control the purity of the hydroquinone desired and to obtain a product which can meet high-purity requirements.

In accordance with the process of the invention and according to the chosen embodiment capable of comprising a different sequence of the stages, it is possible to vary the purity of the product obtained.

There has now been found, and it is this which constitutes the subject matter of the present invention, a process for the preparation of hydroquinone starting from a crude hydroquinone, characterized in that it comprises at least the following stages:

a) the crude hydroquinone in a liquid form, comprising at least resorcin and pyrogallol as impurities, is subjected to a controlled cooling which ensures the crystallization of the pure hydroquinone,
b) separation of the pure hydroquinone crystals from the mother liquors,
c) reheating and partial melting,
d) complete melting of the purified hydroquinone, and
e) recovery of the purified hydroquinone.

According to the invention, a hydroquinone is obtained which has a purity more or less improved according to the type of embodiments of the invention.

The exact composition of the crude hydroquinone $HQ^0$ treated according to the stages of the process of the invention can vary to a fairly large extent. The process of the invention is particularly well suited to crude hydroquinones having complete contents of impurities of the order of 0.5% to 6% by weight, for example 0.5% to 4% by weight, in particular of 1% to 3% by weight, with respect to the total weight of the crude hydroquinone.

However, the invention can also apply to crude hydroquinones which are richer in impurities, above 10% of impurities.

The term "heavy" impurities is understood to mean an impurity having a molecular weight greater than that of hydroquinone and the term "light" impurity is understood to mean an impurity having a molecular weight less than or equal to that of hydroquinone.

Typically, a crude hydroquinone $HQ^0$ treated according to the invention comprises from 0.1 to 4% by weight, for example from 0.2 to 3% by weight, of "light" impurities composed essentially of hydroquinone isomers, namely resorcin and optionally residual pyrocatechol.

Furthermore, in the crude hydroquinone $HQ^0$, the amount of "heavy" impurities, the most important of which is composed of pyrogallol, is usually from 0.1 to 4% by weight, for example from 0.2 to 3% by weight.

A crude hydroquinone $HQ^0$ which is particularly suited to the process of the invention comprises, by weight, with respect to the total amount of crude hydroquinone:

from 94 to 99.5% of hydroquinone,
from 0.1 to 4%, for example from 0.2 to 3%, of resorcin,
from 0.1 to 4%, for example from 0.2 to 3%, of pyrogallol,
optionally pyrocatechol in the form of traces, for example
from 10 to 100 ppm, preferably between 10 and 20 ppm.

In the present invention, the term "hydroquinone" is understood to mean 1,4-dihydroxybenzene (CAS RN 123-31-9) with a melting point of 172° C.±1° C., the term "resorcinol" is understood to mean 1,3-dihydroxybenzene (CAS RN 108-46-3) with a melting point of 110° C.±1° C. and the term "pyrogallol" is understood to mean 1,2,3-trihydroxybenzene (CAS RN 87-66-1) with a melting point of 133° C.±1° C. Melting points are indicated in particular in "Ullmann's Encyclopedia of Industrial Chemistry (2004), 7th edition, Wiley VCH (electronic version)".

Whatever the exact nature of the crude hydroquinone $HQ^0$ treated according to the process of the invention, the stages of the process of the invention are advantageously carried out under the conditions stated below.

Thus, the purification process of the present invention corresponds to a solvent-free purification by crystallization. The crude hydroquinone, comprising impurities, is introduced into the purification process in the solvent-free liquid form, that is to say in the molten state.

This purification technique is known and is generally referred to as "refining", "melt bath recrystallization" or simply "melt recrystallization" or also "MSC" (Melt Static Crystallization).

Such a technique is not, however, known for the purification, to different degrees of purity, of crude hydroquinone comprising both light and heavy impurities of dihydroxybenzene and trihydroxybenzene type, in particular resorcin with pyrogallol and optionally pyrocatechol.

The process according to the invention exhibits the advantage of being easily implemented industrially, with relatively low costs in comparison with the processes currently used today. In addition, the process of the invention makes it possible to obtain hydroquinone of high purity without resorting to the processes conventionally used, such as distillation or also recrystallization in a solvent medium, which use a large amount of energy and/or require the use of large amounts of solvent.

The process according to the invention makes it possible to obtain hydroquinone of high purity, in particular comprising less than 3% by weight, advantageously less than 2% by weight, generally less than 1% by weight, to a few hundred ppm (by weight) of impurities, and even a few tens of ppm (by weight) of impurities.

Furthermore, the process of the invention makes it possible to very strongly reduce the amounts of, indeed even to eliminate, the impurities of dihydroxybenzene type, such as resorcinol, simultaneously with the impurities of trihydroxybenzene type, such as pyrogallol.

According to a preferred embodiment of the invention, the oxygen is removed beforehand from the chamber in which the purification operation is carried out. Thus, the feeding with hydroquinone in the liquid state is carried out in an atmosphere freed from oxygen.

According to one embodiment of the invention, an atmosphere of inert gases is established in the chamber. Recourse may be had to a rare gas, preferably argon, but it is generally preferable to use nitrogen due to its lower cost. Once the inert atmosphere has been established, the hydroquinone in the liquid state is introduced into the crystallizer.

It is possible to envisage feeding hydroquinone in the liquid state originating directly from a manufacturing line.

It is also possible to provide a stage of a process of the invention which consists in melting the hydroquinone. To this end, the product is heated to its melting point. Preferably, the crude hydroquinone is brought to a temperature slightly greater than the melting point of hydroquinone, preferably greater by 5° C. with respect to its melting point and more preferably greater by 5° C. to 30° C. with respect to its melting point.

The temperature to which the crude hydroquinone is brought is chosen between 175° C. and 200° C., preferably between 178° C. and 195° C., advantageously between 180° C. and 185° C. These same temperature ranges are applied for crude hydroquinone in the liquid state originating directly from a manufacturing line.

The melting operation is carried out generally with stirring and can be carried out in a stirred and heated vessel. Heating is advantageously carried out by circulating steam or an appropriate heat-exchange fluid in the jacket.

Mention may in particular be made, as heat-exchange fluids suitable for the invention, of heavy esters of carboxylic acids (for example octyl phthalate), aromatic ethers, such as biphenyl oxyde and/or benzyl oxide, diphenyl, terphenyls, other polyphenyls which are optionally partially hydrogenated, paraffinic and/or naphthenic oils, petroleum distillation residues, silicone oils, and the like.

In accordance with the process of the invention, crude hydroquinone (originating directly from a manufacturing line or else having been subjected to a melting operation) is introduced in the molten state into a crystallizer placed beforehand under an inert atmosphere, as indicated above.

The crystallizer can be of any type known per se as indicated below, according in particular to whether the process is carried out continuously or batchwise, and optionally has available a stirring system. It is possible to operate in a static molten medium (without stirring or circulation of the liquid phase) or in a dynamic molten medium (circulation of the liquid in a loop, falling film technique or others).

In all cases, the crystallizer is equipped with a system which makes possible both the controlled heating and the controlled cooling of the entities present inside the crystallizer. Recourse is generally had to a system for circulation of a heat-exchange fluid in a jacket and/or to a system of heat exchanger type, comprising tubes, plates, disks, and the like.

Use will be made, as heat-exchange fluids suitable for the invention, of the fluids commonly used for these purposes, in particular fluids with a high boiling point, at least greater than 200° C., indeed even than 250° C., which have an appropriate viscosity within the range of temperatures employed during the process of the invention.

By way of examples, use may advantageously be made, as heat-exchange fluids, of those listed above relating to the heating of the vessel used for the optional melting of the hydroquinone.

The devices, in particular the crystallizer, used for the process of the present invention are known and can be of all types known per se, for example those which can be used in the Proabd® MSC process, in particular the crystallizer for crystallization in a molten medium sold by Sulzer (cf. http://www.sulzerchemtech.com) or by Covalence (Saint-Amand-les-Eaux, France).

The first stage of the process consists of a controlled cooling of the crude molten hydroquinone ($HQ^0$) according to a "decrease in temperature/time gradient" curve (see example 1) according to a hydroquinone/impurity(ies) phase diagram drawn up beforehand. This is because it has been discovered that it is possible to construct phase diagrams between pure hydroquinone and the impurities present therein.

These phase diagrams exhibit a eutectic point for hydroquinone/resorcinol, a eutectic point for hydroquinone/pyrogallol, a eutectic point for resorcinol/pyrogallol and a eutectic point for hydroquinone/resorcinol/pyrogallol. The latter point, referred to more simply as "eutectic point" subsequently, corresponds to a temperature which is referred to as "inversion temperature" in the continuation of the present account.

This inversion temperature is lower than the temperature of molten $HQ^0$ and generally lies between 80° C. and 100° C., advantageously between 90° C. and 95° C., for example in the vicinity of 95° C., for crude hydroquinones comprising from 0.5% to 6% of impurities as defined above.

The duration of this first stage of cooling down to the inversion temperature can vary within wide limits depending on whether the temperature gradients (difference in temperature between the crystallizer (heat-exchange fluid) and the molten mass) are small or large.

For example, in the case of "dynamic" processes, where the temperature gradients are generally large, the duration of the first stage can generally vary from a few minutes to a few hours (1 or 2 hours, for example). In the case of static processes, a relatively slow cooling, for example of the order of to 15 hours, advantageously of the order of 8 to 12 hours, generally of the order of 10 hours, is generally carried out.

Due to its slow solidification, the cooling of the molten mass results in the appearance of crystals of purified hydroquinone, that is to say comprising a reduced amount of impurities (with respect to $HQ^0$). At the inversion temperature, the crystallizer comprises crystals of purified hydroquinone and a residual liquid phase (mother liquors) concentrated in impurities.

At this stage of the process, the mixture of crystals and of liquid is advantageously but not necessarily maintained at the inversion temperature for a time sufficient to achieve thermal equilibrium and to minimize the final supersaturation. This time can vary according to whether the process is carried out under static or dynamic conditions, as indicated above, and is generally between a few minutes and 4 hours, for example approximately 2 hours, in the case of processes carried out in static mode.

It is also possible to promote the crystallization, indeed even to control the formation and the porosity of the crystal lattice, for example by creating a cold spot or also by introducing crystallization seeds at a content preferably of less than 2%. Use is made, as crystallization seeds, of a small amount of crystalline hydroquinone originating, for example, from a preceding manufacturing operation and optionally of the appropriate particle size.

In the second stage of the process of the invention, the hydroquinone crystals are separated from the mother liquors. This separation is carried out according to conventional liquid-solid separation techniques known to a person skilled in the art and mention may be made, as such, for example, of separation by gravity flow or mechanical separation, such as filtration, centrifuging or draining, or also by pressurizing with an inert gas (generally nitrogen), this final technique making possible desaturation/filtration of the liquid retention impregnating the crystal lattice, that is to say promoting the removal of the impure liquid phase present in the crystals.

A solid/liquid separation technique entirely suited to the process of the present invention is separation by gravity flow.

The separation stage is generally carried out at the temperature of the end of crystallization, that is to say at the inversion temperature. However, a different temperature can be chosen, although this does not represent a preferred embodiment of the invention.

The third stage of the process consists in reheating the crystallizer in a controlled manner from the inversion temperature up to the melting point of pure hydroquinone (172° C.) or else just above the melting point from 173 to 174° C. and in partially melting the pure hydroquinone crystals impregnated by retention of impure liquid phase. The term used here is sweating: the purity of the liquid phase drawn off continuously increases continuously: its purity describes overall the liquidus of the liquid/solid phase diagram.

The duration of this third stage can also vary within wide limits (depending upon whether the process is static or dynamic, as indicated above) and it is generally carried out for a period of time varying from a few minutes to 12 hours, preferably for 2 to 10 hours, more preferably for approximately 6 hours, in the case of a static process.

When the temperature of 172° C. is reached, the melting stage is carried out by heating to a temperature greater than the partial melting point (172° C.), in order to remelt all the purified hydroquinone crystals. This stage is carried out for a time generally of between a few minutes and 8 hours, more preferably between 1 and 6 hours, in particular for a time of the order of 4 hours.

On conclusion of this complete remelting, the purified hydroquinone is obtained in the liquid form and is recovered, either for immediate use as synthetic reactant, for example, or cooled and formed, according to conventional techniques, in the form of solid objects having a size suitable for handling without risks of dust, typically of the order of at least a few hundred microns to a few millimeters.

This forming can in particular be carried out by employing one or other of the following techniques:
  flaking on a cylinder or on a belt, in which the liquid hydroquinone is brought into contact with a colder metal cylinder or belt and then the film obtained on the cylinder is scraped off with a knife, whereby the solid hydroquinone is recovered in the form of flakes,
  prilling (forming of beads), as described in particular in EP-A-1 556 322, in which the liquid hydroquinone is dispersed in the form of drops in a current of air, for example by dropping it from the top of a tower into a column of air or inert gas, which results in the solid hydroquinone being obtained in the form of beads,
  quenching or shot blasting, where the liquid hydroquinone is dispersed, generally in the form of drops, in a cold immiscible liquid, whereby solid hydroquinone is obtained in the form of granules.

Whatever its final form, the purified hydroquinone obtained according to the process of the invention comprises a very reduced level of impurities, as indicated below.

According to an advantageous embodiment, the purified hydroquinone in the liquid form can again be charged, in whole or in part, to the refining process as just described above, that is to say to a second refining stage. This embodiment makes it possible to further increase the purity of the hydroquinone.

By thus multiplying the refining stages, it is thus possible to access very high levels of hydroquinone purity.

According to another embodiment, it is also advantageous to introduce, into the crystallizer comprising crude hydroquinone $HQ^0$, hydroquinone of intermediate purity $HQ^1$ originating from the same crystallizer (for example, when the process is carried out continuously) or else hydroquinone of intermediate purity originating from a preceding operation. The reference in this case is to "process with recycling".

The amount of hydroquinone of intermediate purity $HQ^1$ introduced with the main feed of crude hydroquinone $HQ^0$ can vary within wide limits. An advantageous recycling ratio $HQ^0/HQ^1$ can, for example, be in the region of 1. An $HQ^0/HQ^1$ ratio of greater than 1, for example in the vicinity of 2, can be envisaged but involves a greater volume to be treated, although it is entirely compatible with an increase in degree of hydroquinone purity obtained. An $HQ^0/HQ^1$ ratio of less than 1, for example in the region of ½, can also be envisaged but exhibits little advantage in view of the increase in degree of hydroquinone purity obtained.

The recycling ratio $HQ^0/HQ^1$ in the vicinity of 1 thus offers a good compromise between increase in degree of purity and volumes to be treated.

According to another advantageous embodiment, the process of the invention can be implemented by combining one or more refining stages and one or more recyclings. It should be noted that the recyclings can be carried out over the same refining stage or also between two or more refining stages.

Thus, the process of the invention can be implemented with two refining stages and a recycling from stage 2 to stage 1, or also with three refining stages and a recycling from stage 3 to stage 2 and/or stage 1, or else with four refining stages and recycling from stage 4 to stage 3 and/or recycling from stage 2 to stage 1 and/or recycling from stage 4 to stage 1, and the like.

As indicated above, the refining operations employing the process of the invention can be carried out continuously or batchwise. According to a continuous implementation, several static or dynamic crystallizer can thus be arranged in cascade, in series and/or in parallel.

On completion of the process of the invention, which can employ one or more refining stage(s), with or without recycling(s), purified hydroquinone is obtained, the characteristics of which are as follows:
  the hydroquinone content is greater than 97%, advantageously greater than 98%,
  the resorcinol content is less than 8000 ppm, preferably less than 4000 ppm, more preferably less than 400 ppm, indeed even less than 100 ppm, and
  the pyrogallol content is less than 8000 ppm, preferably less than 4000 ppm, more preferably less than 400 ppm, indeed even less than 100 ppm.

By way of examples, it is possible to obtain hydroquinone:
  with a degree of purity equal to or greater than 98%, indeed even equal to or greater than 99%,
  with a process employing one refining stage, without recycling,
  with a degree of purity equal to or greater than 99.58% with a process employing one refining stage, with one internal recycling,
  with levels of impurities of less than 200 ppm, indeed even of less than 150 ppm, with a process employing two refining stages and internal recyclings.

The diphenol and pyrogallol contents are determined by high performance liquid chromatography.

Thus, the process of the invention is particularly advantageous as it makes it possible to obtain hydroquinone with different degrees of purity which range between at least 98% and which can be approximately 100%.

BRIEF DESCRIPTION OF THE DRAWINGS

The appended

FIG. 1 diagrammatically represents an embodiment of the process of the invention employing one refining stage, in which:
  1: crude HQ feed
  2: impure HQ residues
  3: pure HQ product.

FIG. 2 is a diagram of an embodiment with one refining stage and recycling of an HQ fraction of intermediate purity, in which:
  1: crude HQ charge
  2: impure HQ residues
  3: intermediate purity HQ recycling
  4: pure HQ product
  5: crude HQ feed 1+intermediate purity HQ recycling (3)

FIG. 3 diagrammatically represents another embodiment of the process of the invention employing two refining stages, with two internal recyclings at each of the two stages, and also a recycling from stage 2 to stage 1. In this embodiment:
1: crude HQ charge) (HQ$^0$)
2: 1st stage impure HQ residues
3: 1st stage intermediate purity HQ recycling
4: 1st stage pure HQ product to 2nd stage feed
5: 1st stage feed: HQ$^0$ (1)+1st stage intermediate purity HQ recycling (3)
6: 2nd stage feed: 1st stage pure HQ (4)+2nd stage intermediate purity HQ recycling (7)
7: 2nd stage intermediate purity HQ recycling to 2nd stage feed
8: 2nd stage impure HQ residues recycling to the n+1 operation, 1st stage
9: 2nd stage high purity HQ product The exemplary embodiments of the invention which follow are given by way of illustration and do not have any limiting nature.

EXAMPLES

Example 1

Purification Thermal Cycle and Experimental Characteristic 1000 g of crude molten hydroquinone) (HQ$^0$), comprising a total of 5% by weight of impurities (resorcin 2.5% by weight, pyrogallol 2.5% by weight), are charged to a 1.5 liter crystallizer maintained at a temperature of 185° C.

The first stage consists of a controlled cooling from 185° C. to 95° C. in 10 hours; crystallization begins from 167° C.

The second stage, of stabilization, with a duration of 2 hours, is carried out at the inversion temperature of 95° C. in order to achieve thermal equilibrium and to minimize the final supersaturation.

The third stage, with a duration of 2 hours, is the draining at the inversion temperature of 95° C. and consists in withdrawing the residual liquid phase concentrated in impurities.

The fourth stage, with a duration of 6 hours, the sweating, consists in reheating the crystallizer in a controlled manner from 95° C. to 172° C. and in partially melting the pure hydroquinone crystals impregnated by retention of impure liquid phase. The withdrawal operation is split up so as to establish, after chemical analysis of the various fractions, an experimental characteristic of the purification, where the purity of the product is represented as a function of the degree of recovery of the initial charge.

The fifth stage is the melting stage, with a duration of 4 hours; it is carried out starting from 172° C.; all the pure hydroquinone crystals are remelted.

TABLE 1

| Purification experimental characteristic | | | |
|---|---|---|---|
| Degree of recovery of the charge (% by weight) | Total concentration of impurities (% by weight) | Resorcin concentration (% by weight) | Pyrogallol concentration (% by weight) |
| 100.0 | 5.00 | 2.50 | 2.50 |
| 98.7 | 4.07 | 2.04 | 2.04 |
| 98.1 | 3.64 | 1.82 | 1.82 |
| 97.8 | 3.43 | 1.72 | 1.72 |
| 96.8 | 2.75 | 1.38 | 1.38 |
| 95.8 | 2.15 | 1.08 | 1.08 |
| 95.0 | 1.74 | 0.87 | 0.87 |
| 93.8 | 1.24 | 0.62 | 0.62 |

TABLE 1-continued

| Purification experimental characteristic | | | |
|---|---|---|---|
| Degree of recovery of the charge (% by weight) | Total concentration of impurities (% by weight) | Resorcin concentration (% by weight) | Pyrogallol concentration (% by weight) |
| 91.8 | 0.83 | 0.415 | 0.415 |
| 86.8 | 0.512 | 0.256 | 0.256 |
| 61.7 | 0.322 | 0.161 | 0.161 |
| 5.0 | 0.085 | 0.0425 | 0.0425 |

The use of this experimental characteristic makes it possible to draw up various purification programs and variants, with or without recycling and/or breaking the purification into stages, in order to optimize the overall yield of the process, to adjust the chemical quality of the purified hydroquinone (HQ), as a function of variants with regard to the composition of the crude HQ, of the size of the equipment, of the levels of recycled materials and their purities and levels of bled-off materials and their purities.

Example 2

Figure 1:
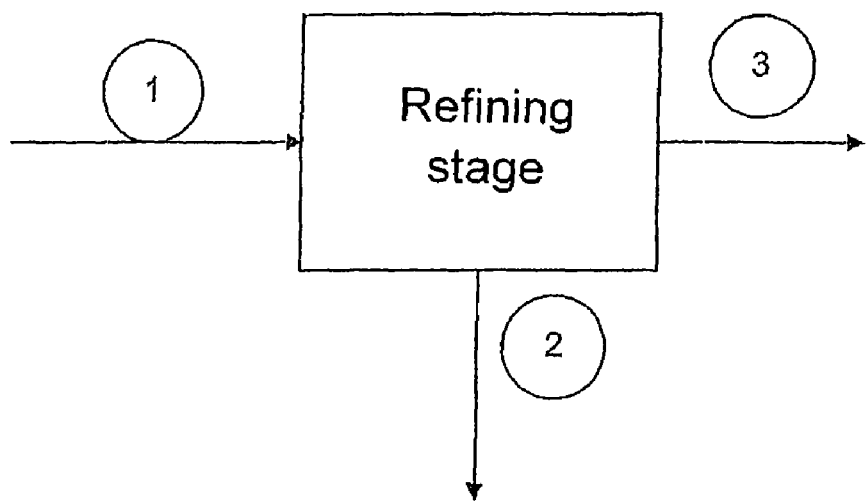
FIGS. 1 to 3 illustrate the invention in order to facilitate the understanding thereof, without, however, limiting the scope thereof.

1-Stage Process without Internal Recycling (FIG. 1)

A crude hydroquinone comprising 4% by weight of total impurities (2% by weight of resorcin, 2% by weight of pyrogallol, traces of pyrocatechin) is purified.

The data of the purification experimental characteristic are combined in the following table 2.

TABLE 2

| Purification experimental characteristic | | | |
|---|---|---|---|
| Degree of recovery of the charge (% by weight) | Total concentration of impurities (% by weight) | Resorcin concentration (% by weight) | Pyrogallol concentration (% by weight) |
| 100.0 | 4.00 | 2.00 | 2.00 |
| 98.7 | 3.26 | 1.63 | 1.63 |
| 98.1 | 2.91 | 1.46 | 1.46 |
| 97.8 | 2.74 | 1.37 | 1.37 |
| 96.8 | 2.20 | 1.10 | 1.10 |
| 95.8 | 1.72 | 0.86 | 0.86 |
| 95.0 | 1.39 | 0.70 | 0.70 |
| 93.8 | 0.994 | 0.497 | 0.497 |
| 91.8 | 0.662 | 0.331 | 0.331 |
| 86.8 | 0.410 | 0.205 | 0.205 |
| 61.7 | 0.258 | 0.129 | 0.129 |
| 5.0 | 0.068 | 0.034 | 0.034 |

The material balance of the purification is presented in table 3 below:

TABLE 3

| Material balance | | | | |
|---|---|---|---|---|
| Stream No. | Nature of the stream | Weight (kg) | Total content of impurities (% by weight) | Pyrogallol content (% by weight) |
| 1 | Crude HQ charge | 1000 | 4.00 | 2.00 |
| 2 | Impure HQ residues | 50 | 53.5 | 26.8 |
| 3 | Pure HQ product | 950 | 1.395 | 0.698 |

Purity of the HQ: 98.605%

Example 3

1-Stage Process without Internal Recycling (FIG. 1)

A crude hydroquinone (HQ⁰) comprising 2% by weight of total impurities (1% by weight of resorcin, 1% by weight of pyrogallol, traces of pyrocatechin) is purified.

Table 4 is obtained according to the process diagram of FIG. 1:

TABLE 4

Material balance

| Stream No. | Nature of the stream | Weight (kg) | Total content of impurities (% by weight) | Pyrogallol content (% by weight) | Resorcin content (% by weight) |
|---|---|---|---|---|---|
| 1 | Crude HQ charge | 950 | 2.00 | 1.00 | 1.00 |
| 2 | Impure HQ residues | 50 | 26.3 | 13.16 | 13.17 |
| 3 | Pure HQ product | 900 | 0.648 | 0.324 | 0.324 |

Purity of the HQ: 99.352%

Example 4

Figure 2:
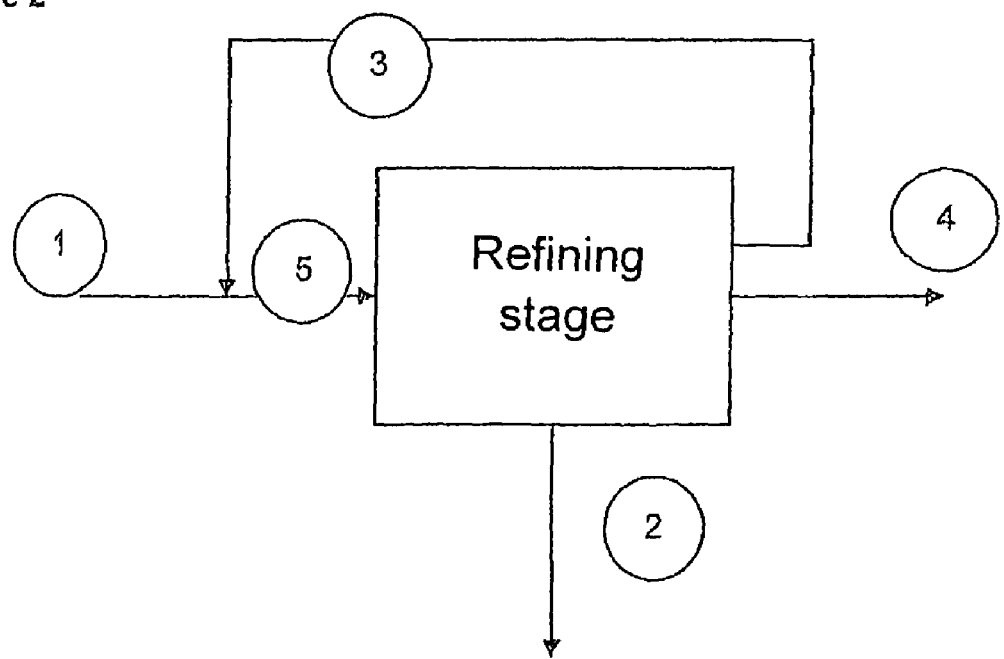

1-Stage Process with Internal Recycling (FIG. 2)

The purification is carried out of a mixture of crude hydroquinone comprising 4% by weight of total impurities (2% by weight of resorcin, 2% by weight of pyrogallol, traces of pyrocatechin) and of hydroquinone recycled from a preceding operation comprising 6.02% by weight of impurities (3.01% by weight of resorcin, 3.01% by weight of pyrogallol).

Table 5 is obtained according to the process diagram of FIG. 2:

TABLE 5

Material balance

| Stream No. | Nature of the stream | Weight (kg) | Total content of impurities (% by weight) | Pyrogallol content (% by weight) | Resorcin content (% by weight) |
|---|---|---|---|---|---|
| 1 | Crude HQ charge | 1000 | 4.00 | 2.00 | 2.00 |
| 3 | Intermediate purity HQ recycling | 1000 | 6.02 | 3.01 | 3.01 |
| 5 | HQ charge + recycling feed | 2000 | 5.01 | 2.50 | 2.50 |
| 2 | Impure HQ residues | 50 | 74.7 | 37.3 | 37.3 |
| 4 | Pure HQ product | 950 | 0.281 | 0.14 | 0.14 |

Purity of the HQ: 99.719%

Example 5

Process Comprising 2 Purification Stages and Internal Recyclings

A mixture of crude hydroquinone (HQ⁰) comprising 4% by weight of total impurities (2% by weight of resorcin, 2% by weight of pyrogallol, traces of pyrocatechin) and of hydroquinone recycled from a preceding operation comprising 6.02% by weight of impurities (3.01% by weight of resorcin, 3.01% by weight of pyrogallol) is purified over a 1st stage.

The pure HQ product from the 1st stage obtained according to Example 4 is introduced with HQ recycled from a 2nd purification stage of a preceding operation. An HQ product of high purity is obtained (<200 ppm of total impurities). The residue from this 2nd stage can be completely recycled to the feed of the 1st stage of the n+1 operation.

Figure 3:
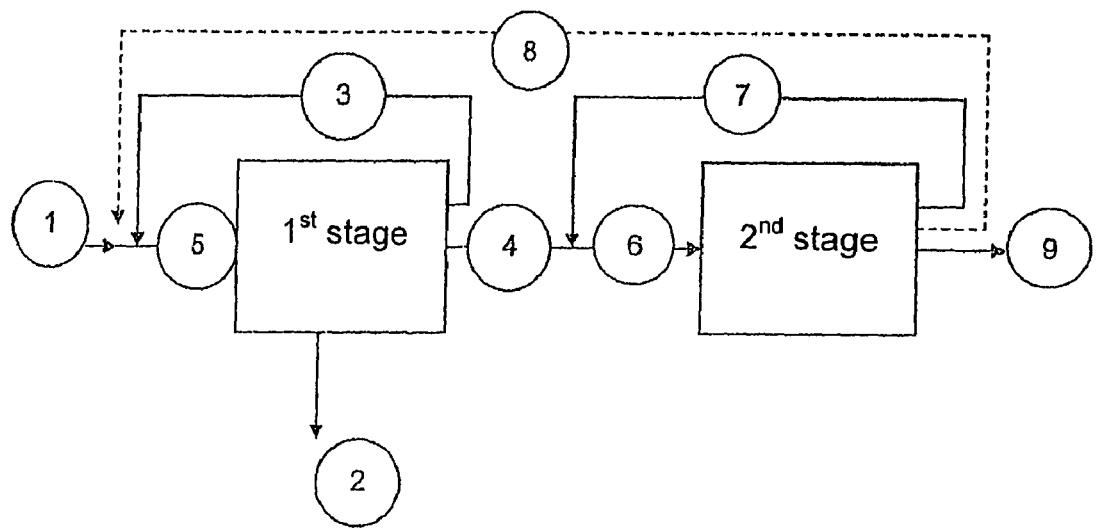

Table 6 is obtained according to the process diagram of FIG. 3:

TABLE 6

Material balance

| Stream No. | Stage No. | Nature of the stream | Weight (kg) | Total content of impurities (% by weight) | Pyrogallol content (% by weight) | Resorcin content (% by weight) |
|---|---|---|---|---|---|---|
| 1 | 1 | Crude HQ charge | 1000 | 4.00 | 2.00 | 2.00 |
| 3 | 1 | Intermediate purity HQ recycling | 1000 | 6.02 | 3.01 | 3.01 |
| 5 | 1 | Charge + recycling 1st stage HQ feed | 2000 | 5.01 | 2.50 | 2.50 |
| 2 | 1 | Impure HQ residues | 50 | 74.7 | 37.3 | 37.3 |
| 4 | 1 | Pure HQ product | 950 | 0.281 | 0.14 | 0.14 |
| 6 | 2 | 2nd stage HQ feed | 1950 | 0.336 | 0.168 | 0.168 |
| 7 | 2 | Intermediate purity HQ recycled material | 1000 | 0.389 | 0.194 | 0.194 |
| 8 | 2 | Intermediate purity HQ residues | 50 | 5.00 | 2.50 | 2.50 |
| 9 | 2 | HQ product of high purity | 900 | <200 ppm | 90 ppm | 90 ppm |

Example 6

Process Comprising 2 Purification Stages and Internal Recyclings

As for example 5, a mixture of crude hydroquinone comprising 4% by weight of total impurities (2% by weight of resorcin, 2% by weight of pyrogallol, traces of pyrocatechin) and of hydroquinone recycled from a preceding operation comprising 6% by weight of impurities (3% by weight of resorcin, 3% by weight of pyrogallol) is purified over a 1st stage.

The pure HQ product from the 1st stage obtained according to example 4 is introduced with HQ recycled from a 2nd purification stage of a preceding operation. The size of the equipment used for this 2nd purification stage is in this instance twice that of the preceding example. An HQ product of high purity is obtained (<150 ppm of total impurities). The residue from this 2nd stage can be completely recycled to the feed of the 1st stage of the n+1 operation.

Table 7 is obtained according to the process diagram of FIG. 3:

TABLE 7

| | | Material balance | | | |
|---|---|---|---|---|---|
| Stream No. | Stage No. | Nature of the stream | Weight (kg) | Total content of impurities (% by weight) | Pyrogallol content (% by weight) | Resorcin content (% by weight) |
| 1 | 1 | Crude HQ charge | 1000 | 4.0 | 2.0 | 2.0 |
| 3 | 1 | Intermediate purity HQ recycling | 1000 | 6.0 | 3.0 | 3.0 |
| 5 | 1 | 1st Stage HQ feed | 2000 | 5.0 | 2.5 | 2.5 |
| 2 | 1 | Impure HQ residues | 50 | 74.7 | 37.3 | 37.3 |
| 4 | 1 | Pure HQ product | 950 | 0.281 | 0.14 | 0.14 |
| 6 | 2 | 2nd stage HQ feed | 3950 | 0.339 | 0.170 | 0.170 |
| 7 | 2 | Intermediate purity HQ recycled material | 3000 | 0.357 | 0.179 | 0.179 |
| 8 | 2 | Intermediate purity HQ residues | 50 | 5.11 | 2.55 | 2.55 |
| 9 | 2 | HQ product of high purity | 900 | <150 ppm | 65 ppm | 65 ppm |

What is claimed is:

1. A process for the preparation of hydroquinone starting from a crude hydroquinone $HQ^0$, comprising a refining stage comprising at least the following stages:

a) controlledly cooling the crude hydroquinone in a liquid form, comprising at least resorcin and pyrogallol as impurities, to effect crystallization of the pure hydroquinone, b) separating the pure hydroquinone crystals from the mother liquors, c) reheating and partially melting said separated crystals, d) completely melting the purified hydroquinone, and e) recovering the purified hydroquinone.

2. The process as defined by claim 1, wherein the crude hydroquinone $HQ^0$ has a content of impurities on the order of 0.5% to 6% by weight, with respect to the total weight of the crude hydroquinone.

3. The process as defined by claim 1, wherein the crude hydroquinone $HQ^0$ comprises from 0.1% to 4% by weight of "light" impurities essentially consisting of hydroquinone isomers, and, optionally, residual pyrocatechol.

4. The process as defined by claim 1, wherein the crude hydroquinone $HQ^0$ comprises from 0.1% to 4% by weight of "heavy" impurities essentially consisting of pyrogallol.

5. The process as defined by claim 1, wherein the crude hydroquinone $HQ^0$ comprises, by weight, with respect to the total amount of crude hydroquinone:
   from 94% to 99.5% of hydroquinone,
   from 0.1% to 4% of resorcin,
   from 0.1% to 4% of pyrogallol, and
   optionally, trace amounts of pyrocatechol.

6. The process as defined by claim 1, wherein stage a) is carried out by controlled cooling of crude molten hydroquinone at a temperature of from 175° C. to 200° C., down to the inversion temperature ranging from 80° C. to 100° C., over a period of time of between 1 and 15 hours.

7. The process as defined by claim 6, wherein stage a) is followed by a period of time sufficient to achieve thermal equilibrium and to minimize the final supersaturation, during which the mixture of crystals and liquid is maintained at the inversion temperature.

8. The process as defined by claim 1, wherein the separation of the pure hydroquinone crystals from the mother liquors is carried out at the inversion temperature.

9. The process as defined by claim 1, wherein the separation of the pure hydroquinone crystals from the mother liquors is carried out by gravity flow.

10. The process as defined by claim 1, wherein the reheating and partial melting stage is carried out starting from the inversion temperature up to the melting point of the pure hydroquinone, over a period of time ranging from 2 to 12 hours.

11. The process as defined by claim 1, wherein the complete melting stage is carried out at a temperature greater than the partial melting temperature, over a period of time ranging from 1 to 8 hours.

12. The process as defined by claim 1, carried out continuously or batchwise, with or without stirring.

13. The process as defined by claim 1, carried out under an inert atmosphere.

14. The process as defined by claim 1, further comprising at least one additional refining stage and the purified hydroquinone obtained in at least one refining stage is introduced in the liquid form into another refining process.

15. The process as defined by claim 1, further comprising at least one additional refining stage, wherein the refining stages are arranged in cascade, in series and/or in parallel.

16. The process as defined by claim 1, further comprising at least one additional refining stage, wherein hydroquinone formed in a refining stage is reintroduced into the same refining stage or is introduced into a preceding refining stage.

17. The process as defined by claim 1, wherein the crude hydroquinone is obtained from a reaction mixture resulting from a hydroxylation of phenol by hydrogen peroxide in the presence of an acid catalyst, optionally after removal of the pyrocatechol by distillation.

18. The process as defined by claim 17, wherein the acid catalyst is selected from the group consisting of:
  strong protic acids,
  sulfonic resins,
  iron(II) and copper(II) complexes, and
  acid zeolites.

19. The process as defined by claim 1, wherein the hydroquinone obtained in step e has a degree of purity equal to or greater than 98% by weight.

20. The process as defined by claim 1, wherein the crude hydroquinone comprises 2% by weight of resorcin, 2% by weight of pyrogallol and trace amounts of pyrocatechin, and wherein the purified hydroquinone has a degree of purity equal to or greater than 98% by weight.

21. The process as defined by claim 1, wherein the crude hydroquinone comprises 1% by weight of resorcin, 1% by weight of pyrogallol and trace amounts of pyrocatechin, and wherein the purified hydroquinone has a degree of purity equal to or greater than 99% by weight.

22. The process as defined by claim 1, further comprising reintroducing hydroquinone formed in the refining stage into the refining stage, wherein the crude hydroquinone comprises 2% by weight of resorcin, 2% by weight of pyrogallol and trace amounts of pyrocatechin, the hydroquinone reintroduced into the refining stage comprises 3.0% by weight of resorcin and 3.0% by weight of pyrogallol, and the recycling ratio is 1, and wherein the purified hydroquinone has a degree of purity equal to or greater than 99.5% by weight.

23. The process as defined by claim 1, further comprising a second refining stage, wherein each of the refining stages introduces purified hydroquinone obtained at the end of the refining stage into step a) of the same refining stage, the crude hydroquinone comprises 2% by weight of resorcin, 2% by weight of pyrogallol and trace amounts of pyrocatechin, the hydroquinone reintroduced into the refining stage comprises 3.0% by weight of resorcin and 3.0% by weight of pyrogallol, and the recycling ratio is 1, and wherein the purified hydroquinone has less than 200 ppm of total impurities.

24. The process as defined by claim 1, further comprising a second refining stage wherein each of the refining stages introduces purified hydroquinone obtained at the end of the refining stage into step a) of the same refining stage, wherein the crude hydroquinone comprises 2% by weight of resorcin, 2% by weight of pyrogallol and trace amounts of pyrocatechin, the hydroquinone recycled from a preceding operation comprises 3% by weight of resorcin and 3% by weight of pyrogallol, and the recycling ratio being equal to 3, and wherein the purified hydroquinone has less than 150 ppm of total impurities.

* * * * *